US006604902B2

(12) United States Patent
Norris et al.

(10) Patent No.: US 6,604,902 B2
(45) Date of Patent: *Aug. 12, 2003

(54) CARTRIDGE LOADER AND METHODS

(75) Inventors: Michael C. Norris, Santa Clara, CA (US); Peter Lobban, Los Altos, CA (US); Donald Besemer, Los Altos, CA (US); Andrew B. Carlson, Atherton, CA (US)

(73) Assignee: Affymetrix, Inc., Santa Clara, CA (US)

( * ) Notice: Subject to any disclaimer, the term of this patent is extended or adjusted under 35 U.S.C. 154(b) by 52 days.

This patent is subject to a terminal disclaimer.

(21) Appl. No.: 10/180,588

(22) Filed: Jun. 26, 2002

(65) Prior Publication Data

US 2002/0164235 A1 Nov. 7, 2002

Related U.S. Application Data

(63) Continuation-in-part of application No. 09/691,702, filed on Oct. 17, 2000.
(60) Provisional application No. 60/217,246, filed on Jul. 10, 2000.

(51) Int. Cl.[7] ............................................. G01N 35/00
(52) U.S. Cl. ............................ 414/331.05; 414/331.15; 414/806
(58) Field of Search ..................... 414/180, 222.07, 414/331.01–331.04, 937, 941, 331.05, 331.15, 806

(56) References Cited

U.S. PATENT DOCUMENTS

| 4,665,034 A | 5/1987 | Chandler ..................... 435/287 |
| 4,829,010 A | 5/1989 | Chang ........................... 422/58 |
| 4,859,419 A | 8/1989 | Marks et al. .................. 422/56 |
| 5,104,808 A | 4/1992 | Laska et al. .................. 436/48 |
| 5,143,854 A | 9/1992 | Pirrung et al. ............... 436/518 |
| 5,154,888 A | 10/1992 | Zander et al. ................. 422/58 |
| 5,229,297 A | 7/1993 | Schniplesky et al. ......... 436/94 |
| 5,230,866 A | 7/1993 | Shartle et al. ............... 422/103 |
| 5,233,844 A | * 8/1993 | Knippscheer et al. ......... 62/440 |
| 5,258,781 A | 11/1993 | John ........................... 346/140 |

FOREIGN PATENT DOCUMENTS

| WO | WO 89/10977 | 11/1989 | ............ C12Q/1/68 |
| WO | WO 89/11548 | 11/1989 | ............ C12Q/1/68 |
| WO | WO 90/15070 | 12/1989 | ............ C07K/1/04 |
| WO | WO 92/10092 | 6/1992 | |
| WO | WO 93/09668 | 5/1993 | |
| WO | WO95/33846 | 12/1995 | ............ C12Q/1/00 |

OTHER PUBLICATIONS

Fodor et al., "Light–Directed, Spatially Addressable Parallel Chemical Synthesis," *Science,* 251:767–777 (1991) (Note: This reference is located in parent case 08/624,312).

*Physical Acoustics, Principles and Methods,* vol. 2, Part B, Mason, ed., Academic Pres, (1965) (Note: This reference is located in the parent case 08/624,312).

*Piezoelectric Technology, Data for Engineers,* Clevite Corp. (Note: This reference is located in the parent case 08/624, 312).

Agilent Technologies Press Release, *Agilent Technologies Announces Launch of Next Generation Fully Automated DNA Microarray Scanner,* Palo Alto, California, Jun. 25, 2001.

Agilent Technologies, *Agilent Microarray Scanner,* U.S.A. Aug. 6, 2001.

*Primary Examiner*—Eileen D. Lillis
*Assistant Examiner*—Charles A. Fox
(74) *Attorney, Agent, or Firm*—Townsend and Townsend and Crew LLP

(57) ABSTRACT

A device for transporting cartridges comprises a housing for holding a plurality of cartridges in a temperature controlled environment. A transport system is also provided and has a grasping mechanism for grasping one of the cartridges. The transport system is further used to remove the cartridge from the housing and to place the cartridge into a scanner.

45 Claims, 15 Drawing Sheets

U.S. PATENT DOCUMENTS

| | | | |
|---|---|---|---|
| 5,279,721 A | 1/1994 | Schmid | 204/182.8 |
| 5,288,463 A | 2/1994 | Chemelli | 422/58 |
| 5,296,195 A | 3/1994 | Pang et al. | 422/82.05 |
| 5,384,261 A | 1/1995 | Winkler et al. | 436/518 |
| 5,422,271 A | 6/1995 | Chen et al. | 435/287 |
| 5,424,186 A | 6/1995 | Fodor et al. | 536/22.1 |
| 5,436,129 A * | 7/1995 | Stapleton | 435/6 |
| 5,459,325 A * | 10/1995 | Hueton et al. | 250/458.1 |
| 5,486,335 A | 1/1996 | Wilding et al. | 422/55 |
| 5,489,678 A | 2/1996 | Fodor et al. | |
| 5,500,187 A | 3/1996 | Deoms et al. | 422/58 |
| 5,543,329 A | 8/1996 | Bedell | 435/7.32 |
| 5,578,832 A | 11/1996 | Trulson et al. | 250/458.1 |
| 5,585,639 A * | 12/1996 | Dorsel et al. | 250/458.1 |
| 5,587,128 A | 12/1996 | Wilding et al. | 422/250 |
| 5,593,838 A | 1/1997 | Zanzucchi et al. | 435/6 |
| 5,593,839 A | 1/1997 | Hubbell et al. | 435/6 |
| 5,595,908 A | 1/1997 | Fawcett et al. | 435/287.2 |
| 5,599,504 A | 2/1997 | Hosoi et al. | 422/82.08 |
| 5,627,041 A | 5/1997 | Shartle | 435/7.24 |
| 5,635,358 A | 6/1997 | Wilding et al. | 435/7.2 |
| 5,637,469 A | 6/1997 | Wilding et al. | 435/7.2 |
| 5,652,149 A | 7/1997 | Mileaf et al. | 436/518 |
| 5,658,802 A | 8/1997 | Hayes et al. | 436/518 |
| 5,674,743 A | 10/1997 | Ulmer | 435/287.2 |
| 5,675,700 A | 10/1997 | Atwood et al. | 392/382 |
| 5,683,916 A | 11/1997 | Goffe et al. | 436/535 |
| 5,698,450 A | 12/1997 | Ringrose et al. | 436/526 |
| 5,716,825 A | 2/1998 | Hancock et al. | 435/286.5 |
| 5,726,010 A | 3/1998 | Clark | 435/5 |
| 5,726,013 A | 3/1998 | Clark | 435/5 |
| 5,945,334 A * | 8/1999 | Besemer et al. | 435/287.2 |
| 5,953,804 A * | 9/1999 | Dragotta | 29/407.1 |
| 5,962,834 A * | 10/1999 | Markman | 235/385 |
| 6,068,437 A * | 5/2000 | Boje et al. | 414/331.02 |
| 6,097,025 A | 8/2000 | Modlin et al. | 250/227.22 |
| 6,395,554 B1 | 5/2002 | Regan et al. | |

* cited by examiner

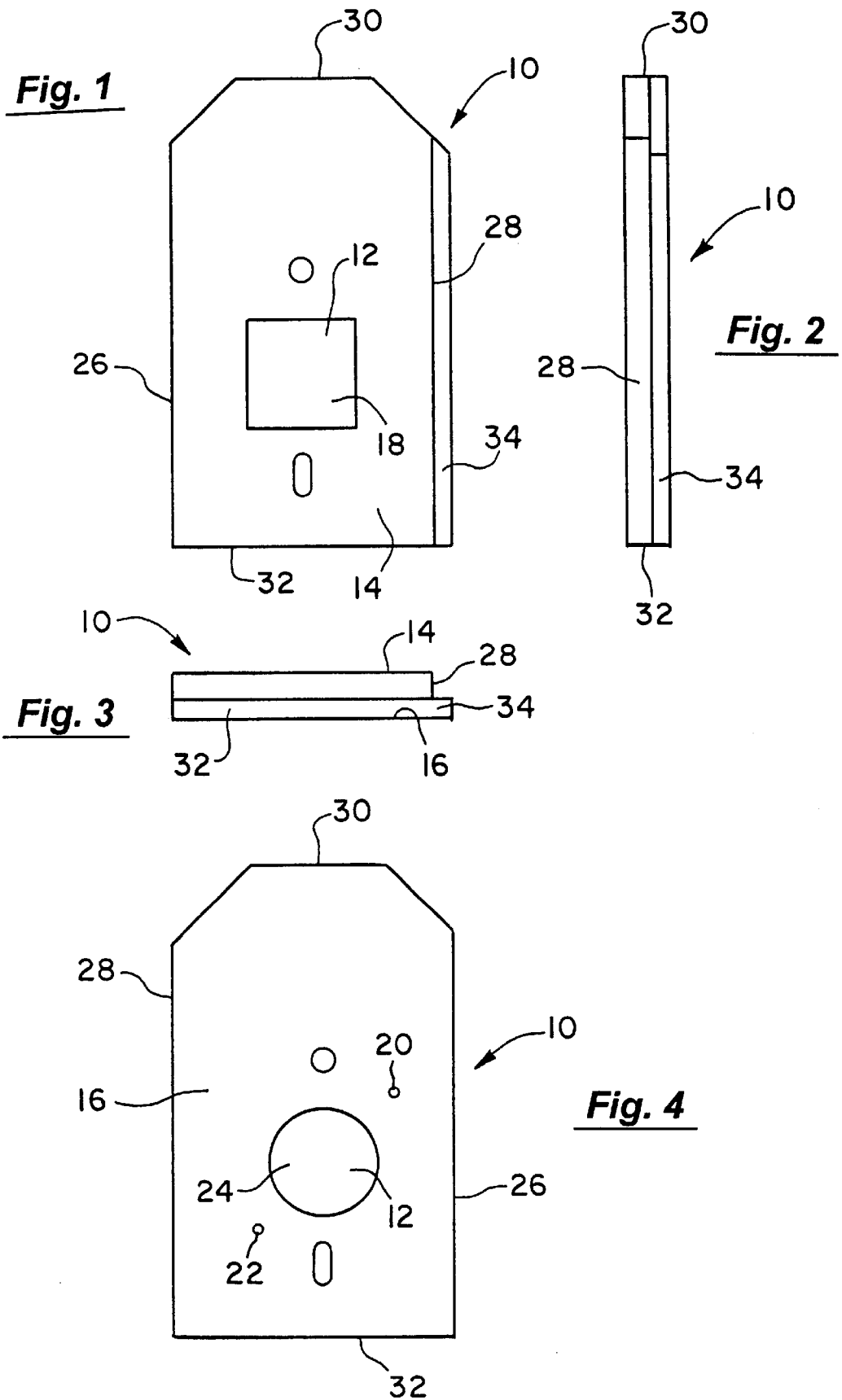

CARTRIDGE LOADER AND METHODS

CROSS REFERENCE TO RELATED APPLICATIONS

This application is a continuation in part application Ser. No. 09/691,702, filed Oct. 17, 2000, and claims the benefit from U.S. Provisional Patent Application No. 60/217,246, filed Jul. 10, 2000, the complete disclosure of which is herein incorporated by reference.

BACKGROUND OF THE INVENTION

This invention relates generally to the field of automation, and in particular to the use of automated equipment to transfer items. More specifically, the invention relates to the automated transfer of array cartridges into and out of an imaging apparatus.

1. Polymer Arrays

Methods for using arrays of polymers to identify receptors with specific affinities for one of the polymers in the array are known. For example, one method uses immobilized antibodies to analyze binding to peptide ligands or vice-versa. Another type of method uses immobilized oligonucleotides to analyze hybridization to a target nucleic acid. For instance, U.S. patent application Ser. No. 08/624,312, filed Mar. 26, 1996, the complete disclosure of which is herein incorporated by reference, describes apparatus and methods for carrying out repeated hybridizations of a target nucleic acid to an array of nucleic acid probes. Such polymer arrays are described in, e.g., U.S. Pat. No. 5,143,854 and published PCT Application Nos. WO90/15070 and WO92/10092, the complete disclosures of which are herein incorporated by reference. These polymer arrays are nucleic acid arrays which include a plurality of different polynucleotides coupled to a substrate in different known locations.

In one exemplary arrangement, such arrays are packaged within a housing or cartridge, like those described in, e.g., U.S. Pat. No. 5,945,334, and in copending U.S. patent application Ser. Nos. 08/624,312, previously incorporated by reference, 08/528,173, filed Sep. 19, 1995, and published PCT Application No. WO95/33846. As described at col. 4, lines 1–11 of U.S. Pat. No. 5,945,334, a probe is a surface-immobilized molecule that is recognized by a particular target and is sometimes referred to as a ligand. Examples of probes that can be investigated by this invention include, but are not restricted to, agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides or nucleic acids, oligosaccharides, proteins, and monoclonal antibodies. The disclosures of all of these references are herein incorporated by reference. In brief, such a cartridge may be constructed of a body having a reaction cavity or hybridization chamber. The array or substrate is mounted over the cavity on the body such that the front side of the array substrate, e.g., the side upon which the polynucleotides are situated, is in fluid communication with the cavity. The cartridge includes inlet and outlet ports to allow various fluids to be introduced into and removed from the hybridization chamber.

2. Imaging

Imaging the polymer arrays may be accomplished, for example, by placing the cartridges into a scanning device, such as the GeneArray scanner, available from Affymetrix, Inc. Techniques for imaging polymer arrays are described in U.S. Pat. Nos. 5,834,758 and 5,578,832, the complete disclosures of which are herein incorporated by reference.

In many cases, it is desirable to maintain the cartridges in a temperature controlled environment. Hence, a need exists for equipment and techniques to transfer cartridges from a temperature controlled environment for placement into the scanner in an organized and efficient manner, and for the return of the cartridges to the temperature controlled environment following imaging. Hence, the invention is related to apparatus and methods to facilitate imaging of array cartridges in such a manner.

SUMMARY OF THE INVENTION

In one embodiment, a device for transporting cartridges comprises a housing for holding a plurality of cartridges in a temperature controlled environment. The device further includes a transport system having a grasping mechanism to grasp one of the cartridges, to remove the cartridge from the housing and to place the cartridge into a scanner. In this way, each cartridge remains within a temperature controlled environment until ready for scanning. At such time, the transport system is employed to remove the cartridge from the housing and to place the removed cartridge into the scanner.

In one aspect, the device further includes a heating station for heating a cartridge (to prevent fogging) prior to insertion into the scanner. As such, the grasping mechanism may be configured to place the grasped cartridge at the heating station prior to placement into the scanner. In one specific aspect, the heating station may include a fan that is disposed to blow ambient air onto the cartridge to heat the cartridge.

In another aspect, the device may also include a holding station to hold a cartridge after being removed from the scanner. In this way, a cartridge that is removed from the scanner may be positioned near the scanner during a cycle where another cartridge is removed from the heating station and placed into the scanner. The cartridge that is held in the holding station may then be placed back into the housing. In this manner, the throughput of the device may be increased by reducing the amount of travel by the grasping system while the scanner is idle, i.e. awaiting a new cartridge.

Conveniently, a rack system may be rotatably disposed within the housing and may include a plurality of racks for holding the cartridges. In one aspect, a plurality of carriers may be provided, with each carrier holding multiple cartridges. In this way, a carrier of cartridges may conveniently be placed into the housing and coupled to the rack system simply by inserting the carrier into one of the racks. Conveniently, a belt may be coupled to the rack system, and a motor may be used to rotate the belt, thereby rotating the rack system. By rotating the rack system, one or more carriers may be aligned with an opening in the housing to facilitate removal of the cartridges. In a particular aspect, the carriers may each have a bottom end and an open top end, and a plurality of slots for receiving the cartridges in a parallel arrangement. When inserted into the slots, the cartridges extend above the top ends of the carriers to facilitate easy gasping and removal from the carriers. Further, the rack system may be configured to maintain the top ends of the carriers generally horizontal during rotation. In this way, the cartridges will not fall out of the carriers when rotated within the housing. Such a feature may be accomplished by use of belts that maintain alignment of the individual racks during rotation by the motor.

In another aspect, the device may include a barcode reader that is disposed within the housing. In this way, barcode labels on the cartridges may be read as they are removed from and/or placed into the housing. In one aspect, the grasping mechanism comprises a pair of fingers that are movable toward and away from each other to grasp and release the cartridges. In still another aspect, the transport system may comprise a horizontal lead screw and a first motor to rotate the horizontal lead screw. With such a configuration, the grasping mechanism may be coupled to the horizontal lead screw such that rotation of the lead screw translates the grasping mechanism horizontally. Further, a vertical lead screw may be provided along with a second motor to rotate the vertical lead screw. The grasping mechanism may be coupled to the vertical lead screw such that rotation of the lead screw translates the grasping mechanism vertically. A controller may then be employed to operate the motors and the grasping mechanism when transporting the cartridges. Conveniently, the housing may include a lid, and an electric motor may be used to open the lid, such as when receiving a signal from the controller. In this way, the housing may remain closed until a cartridge is removed from or placed into the housing. Alternatively, the lid may be slid open and closed by some interaction of the horizontal travelling system and the lid, i.e. the interaction could push the lid to the side.

The invention further provides an alignment mechanism for aligning a scanner with transporting device, such as the transporting device just described. The alignment mechanism comprises a clamping plate that may be clamped to a portion of the scanner. For example, the alignment mechanism may be clamped to a pair of feet on the bottom of the scanner. An adjustment plate is slidably coupled to the clamping plate and has at least one connector that may be connected to the transporting device, thereby coupling the scanner to the transporting device. An alignment fixture is removably coupled to the adjustment plate and includes an arm that is adapted to be aligned with an entry port of the scanner. In this way, the scanner may be moved relative to the transport device until the alignment fixture is aligned with the entry port. A securing mechanism may then be operated to secure the adjustment plate to the clamping plate, thereby fixing the position of the scanner relative to the transporting device. The alignment fixture may then be removed from the adjustment plate. Alternatively, the transporting device and the scanner may be aligned without the use of an alignment mechanism. Hence, the invention is not intended to be limited for use only with an alignment mechanism.

The invention further provides a method for transporting cartridges. According to the method, a plurality of cartridges are placed into a temperature controlled housing. One of the cartridges is grasped and removed from the housing with a grasping mechanism, moved to the scanner and then placed into the scanner. The grasping mechanism is then opened to deposit the cartridge into the scanner.

In one step, the cartridges are rotated within the housing to align groups of the cartridges with an opening in the housing to facilitate removal of the cartridges. In another step, each cartridge is placed in a warming station prior to being deposited into the scanner. For example, ambient air may be blown onto the cartridge to warm the cartridge and preventing fogging of the cartridge when within the scanner. After scanning, the cartridge is removed from the scanner and placed back into the housing, and another cartridge is placed into the scanner.

In an alternative aspect, to increase throughput the cartridge may be placed in a holding station after removal of the cartridge from the scanner. For example, one cartridge may be placed into the scanner prior to replacing a removed cartridge that is held within the holding station back into the housing. In this way, the grasping mechanism may return to the warming station to find a new cartridge for the scanner after removing a cartridge from the scanner. The grasping mechanism may then deposit the new cartridge into the scanner and return the cartridge that is held at the holding station back to the housing. While at the housing, another cartridge may then be removed and placed into the warming station to complete the cycle. In this way, the amount of travel of the grasping mechanism is minimized while the scanner is sitting idle, i.e. awaiting another cartridge, to increase throughput.

In another step, a barcode label on the cartridge may be read upon removal of the cartridge from the housing to keep track of which cartridges have been removed and scanned. In yet another step, the housing is aligned with the scanner and the housing is secured to the scanner prior to use.

In an alternative embodiment, a method for transporting cartridges comprises placing a plurality of cartridges into a carrier such that the cartridges extend above the carrier. One of the cartridges is removed from the carrier with a grasping mechanism and is moved to the scanner. The cartridge is placed into the scanner, and the grasping mechanism is released to deposit the cartridge into the scanner.

BRIEF DESCRIPTION OF THE DRAWINGS

FIG. 1 is a front view of one embodiment of a cartridge.

FIG. 2 is a side view of the cartridge of FIG. 1.

FIG. 3 is an end view of the cartridge of FIG. 1.

FIG. 4 is a rear view of the cartridge of FIG. 1.

DESCRIPTION OF THE SPECIFIC EMBODIMENTS

Figure 5:
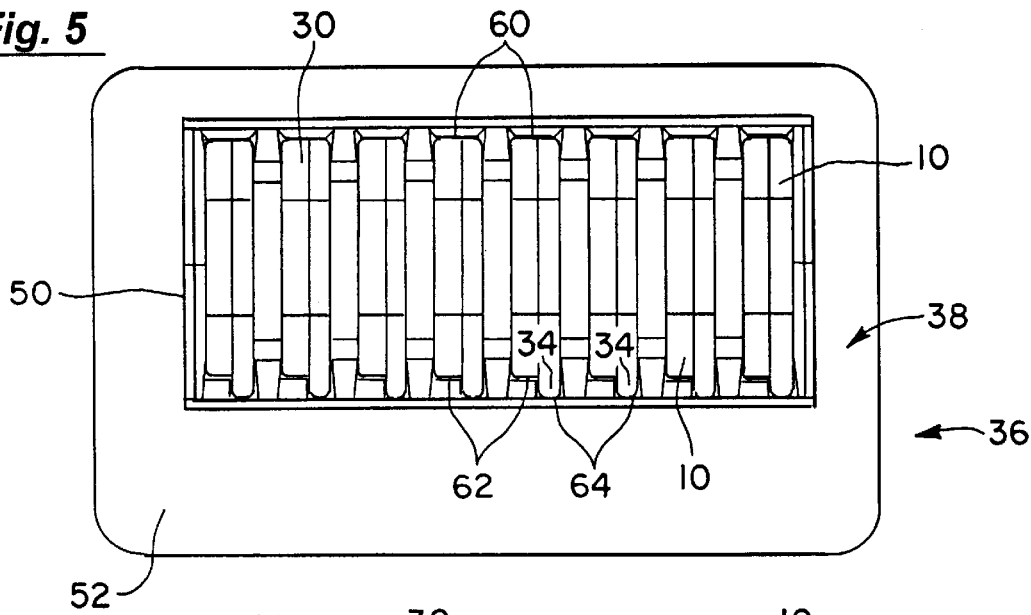
FIG. 5 is a top view of a carrier shown holding a plurality of cartridges according to the invention.

The invention provides for the transport of cartridges into an imaging device or scanner where the probe arrays are imaged. The invention may be used with essentially any type of imaging device or scanner where cartridges are inserted and processed. Conveniently, such scanners may utilize the imaging techniques described in U.S. Pat. Nos. 5,834,758 and 5,578,832, previously incorporated by reference, when imaging the probe arrays. However, the invention may be utilized with other types of scanners as well.

The cartridges used with the invention may be utilized in performing a variety of procedures, including, for example, hybridization reactions and, more specifically, nucleic acid hybridizations, extension or amplification reactions using tethered probes as template or primer sequences, screening of receptors against arrays of small molecules, peptides or peptideomimetics, carbohydrates, and the like. Cartridges suitable for performing such procedures are described in U.S. Pat. No. 5,945,334 and in co-pending U.S. application Ser. Nos. 08/624,312 and 08/528,173 and PCT Application No. WO95/33846, previously incorporated herein by reference. However, it will be appreciated that the invention is not intended to be limited to only these specific types of cartridges.

Referring now to FIGS. 1–4, one embodiment of a cartridge 10 that may be inserted into a scanner will be described. Cartridge 10 includes a chamber 12 containing a fluid. Cartridge 10 further includes a front 14, a rear 16, and a cavity 12 which is defined in part by a generally planar face 18. Positioned across cavity 12 is an array chip (not shown). When the array chip is positioned over cavity 12, a hybridization chamber is formed. The hybridization chamber is generally rectangular or square in geometry and has a narrow depth as defined by the distance between planar face 18 and the array chip. Extending between face 18 and the array chip are sides that intersect with each other to form corners and which further define the chamber. In one specific embodiment, the distance between face 18 and the array chip may be in the range from about 0.5 mm to about 2.0 mm. Further, face 18 may have a length of about 5 mm to about 15 mm and a width of about 5 mm to about 15 mm. An inlet port 20 and an outlet port 22 are included in rear 16 to allow various fluids to be introduced into and removed from the hybridization chamber. Rear 16 further includes a cavity 24, located adjacent the array, which is adapted for receiving a temperature monitoring and/or controlling device.

Cartridge 10 includes a pair of sides 26 and 28, a top 30 and a bottom 32. Extending from side 28 is an edge 34 that permits insertion of cartridge 10 into a carrier in only one orientation as described hereinafter.

Figure 6:
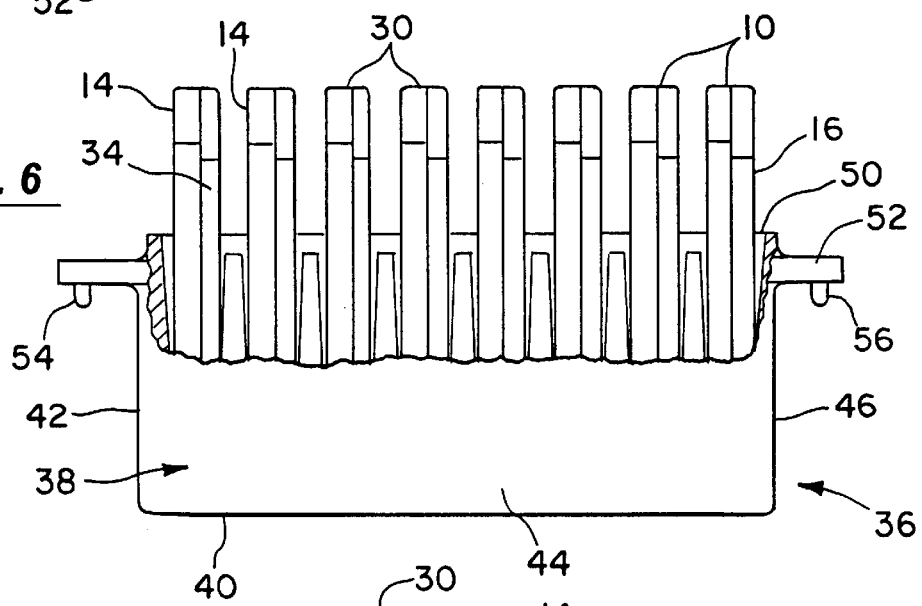
FIG. 6 is a partially cut away side view of the carrier and cartridges of FIG. 5.
Figure 7:
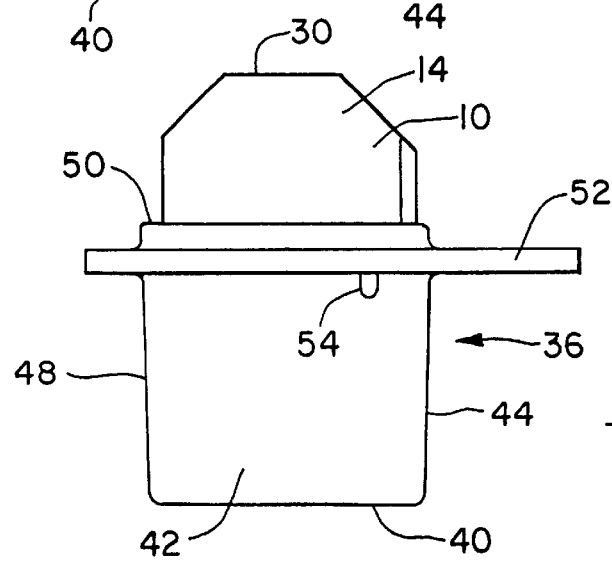
FIG. 7 is an end view of the carrier and cartridges of FIG. 5.

Referring now to FIGS. 5–9, an embodiment of a carrier 36 that may be used to hold a plurality of cartridges will be described. For convenience of illustration, FIGS. 5–7 illustrate carrier 36 holding a plurality of cartridges 10 that are identical to those just described. Carrier 36 comprises a carrier body 38 having a bottom 40, four sides 42, 44, 46 and 48, and a top 50. Extending from the sides is a projection 52 to facilitate coupling of carrier to a rotation device as described hereinafter. Conveniently, projection 52 may be oversized at side 44 to serve as a handle when inserting and removing carrier from other equipment. Further, carrier 36 may include a pair of knobs 54 and 56 to facilitate locking of carrier 36 within other equipment.

Figure 8:
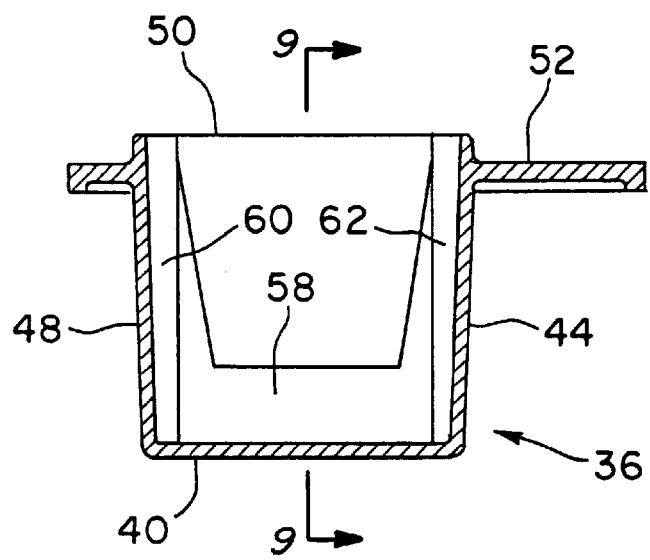
FIG. 8 is a cross sectional end view of the carrier of FIG. 5.
Figure 9:
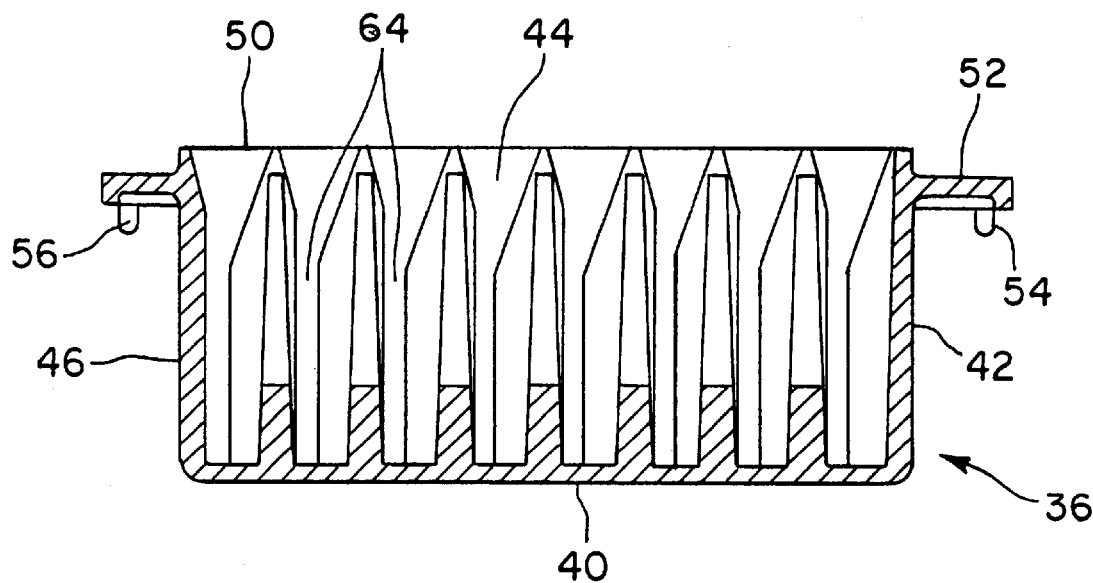
FIG. 9 is a cross sectional side view of the carrier of FIG. 5.

As best shown in FIG. 8, a plurality of walls 58 extend between sides 44 and 48. As shown in FIG. 5, walls 58 define pairs of grooves 60 and 62 into which cartridges 10 are inserted. Grooves 60 define a generally straight channel, while grooves 62 include a keyed notch 64 (see also FIG. 9). Carrier 10 is configured such that cartridges 10 may be received in only one specific orientation. More specifically, edge 34 may be received only within notch 64, and only when front 14 is parallel with side 42. In this way, sides 26 are received into grooves 60, sides 28 are received into grooves 62, and tops 30 of cartridges 10 extend above top 50 of carrier 36, with cartridges 10 each facing the same direction. In this way, the cartridges 10 will be in the same orientation when removed from carrier 36. In this manner, the cartridges may include a barcode label that is scanned with a fixed barcode reader after removal from carrier 36.

Figure 10:
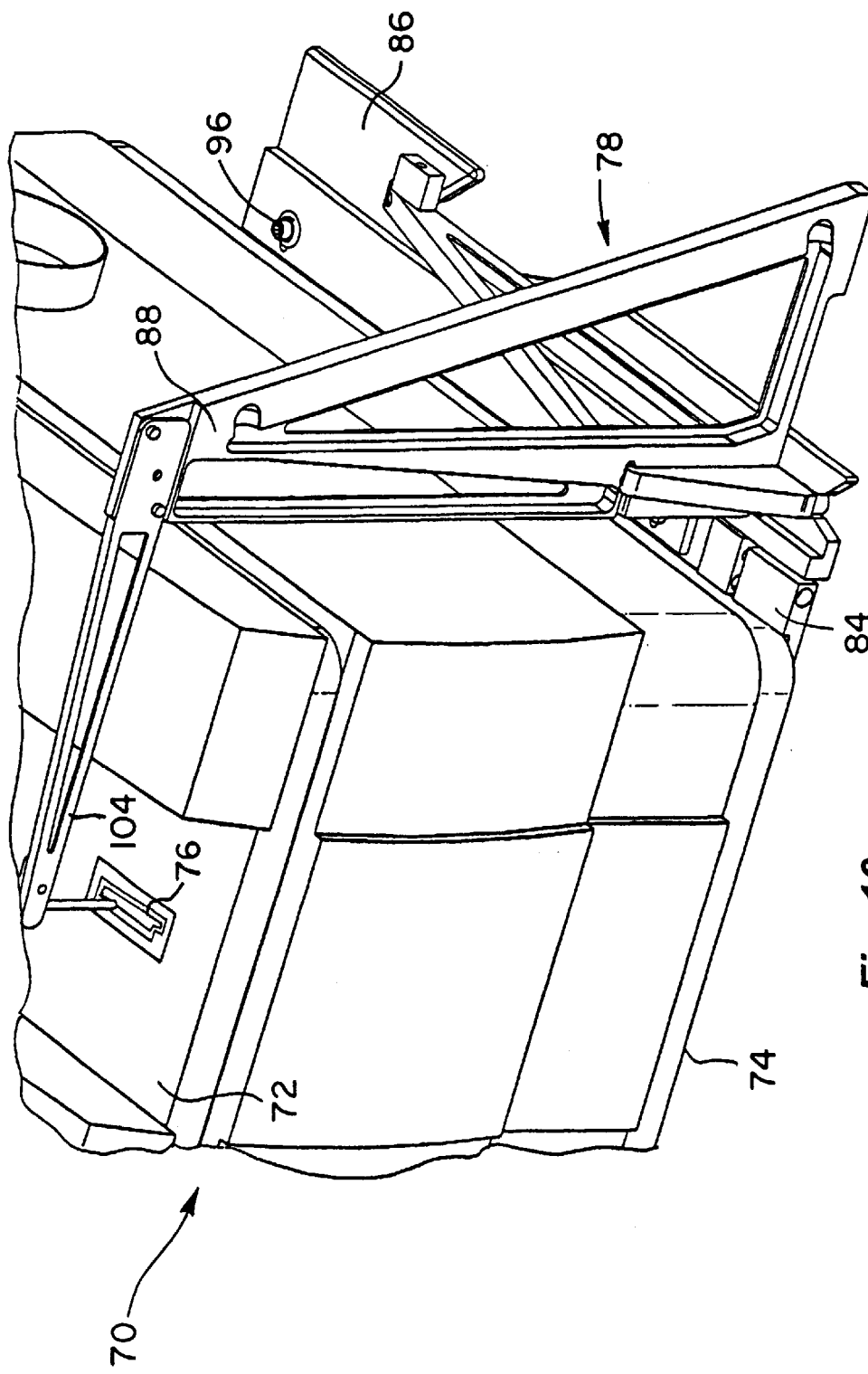
FIG. 10 is a partial top perspective view of a scanner and an alignment mechanism that is coupled to the scanner according to the invention.

FIG. 10 illustrates one embodiment of a scanner 70 that is employed to image probe arrays contained in cartridges, such as cartridge 10 as previously described. Scanner 70 has a top end 72 and a bottom end 74. Top end 72 includes an entry port 76 into which array cartridges are placed in order to scan the cartridges. Conveniently, scanner 10 may be constructed in a manner similar to a GeneArray scanner, manufactured by Hewlett-Packard, and available from Affymetrix, Inc. Such a scanner is constructed such that excessive weight placed on top end 72 may compromise the alignment of the scanner. Accordingly, the invention provides a cartridge transport device that may be coupled to scanner 70 and employed to transfer cartridges into entry port 76 without placing weight onto top end 72 as described in greater detail hereinafter.

Figure 11:
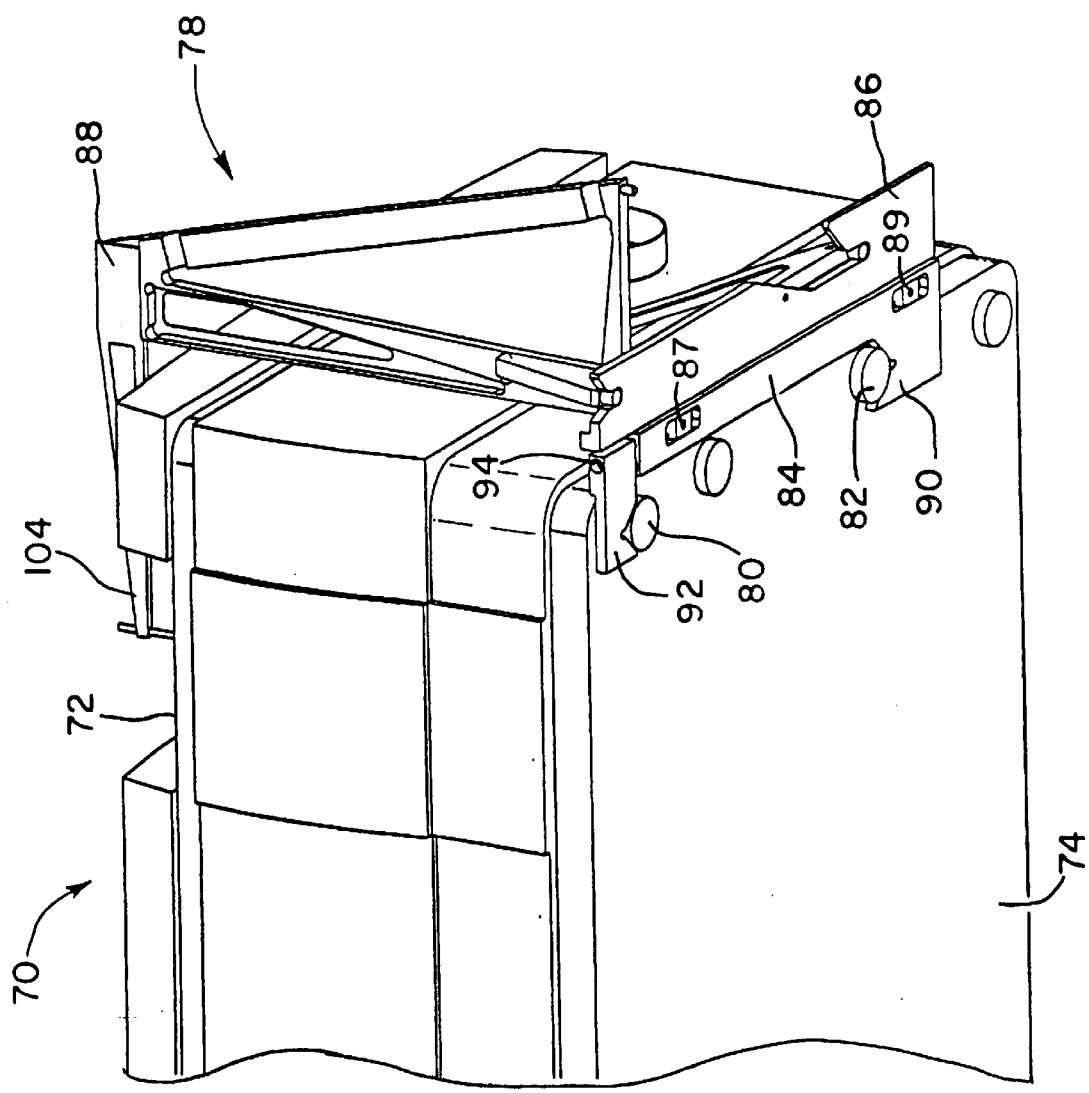
FIG. 11 is a bottom perspective view of the scanner and alignment mechanism of FIG. 10.

As also shown in FIG. 11, an alignment mechanism 78 is coupled to scanner 70 and serves to couple a cartridge transport device to scanner 70 in an aligned configuration. Conveniently, alignment mechanism 78 is constructed to be attached to a pair of feet 80 and 82 on bottom end 74 of scanner 70. In this way, alignment mechanism 78 may be coupled to scanner without posing a threat of damage to the scanner.

Figure 12:
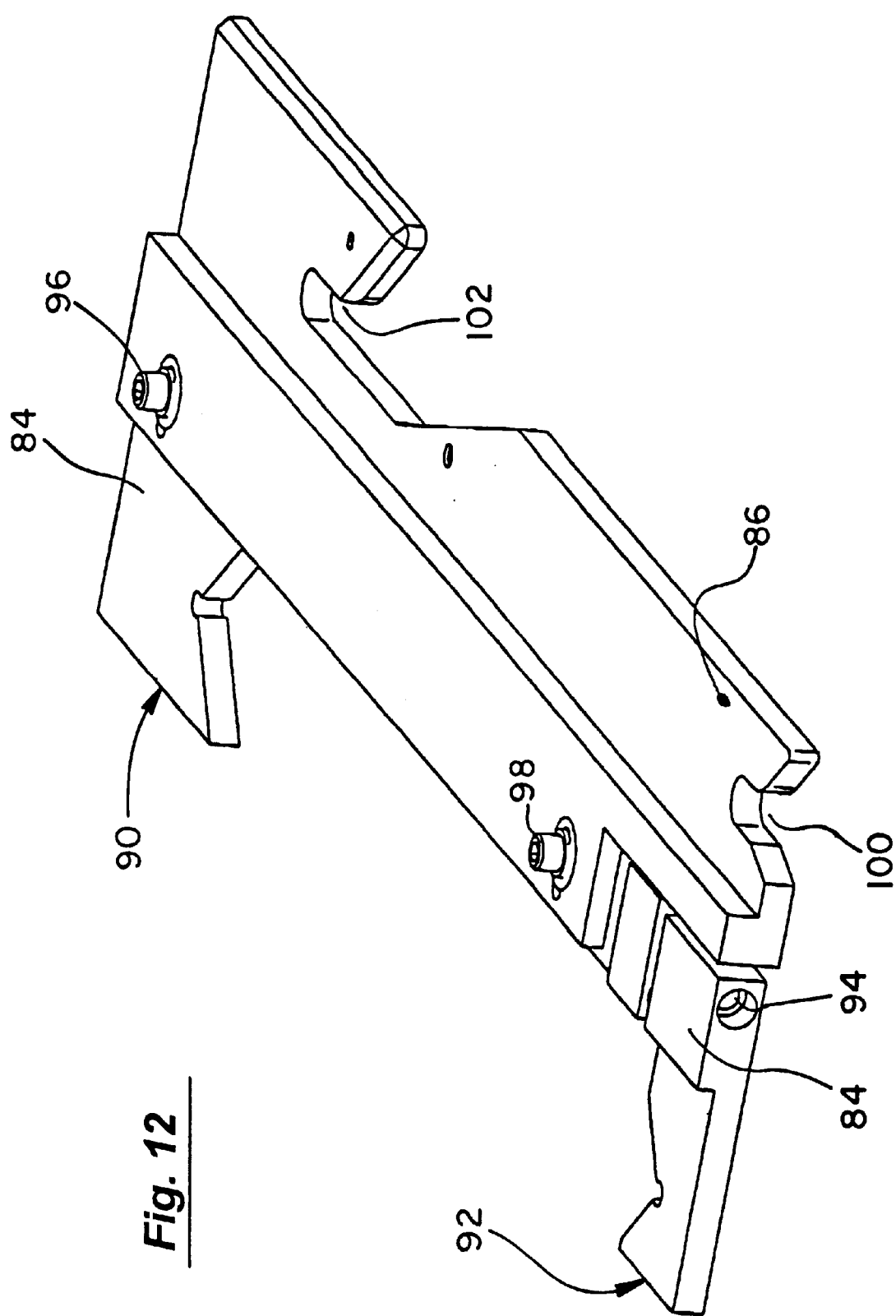
FIG. 12 is a top perspective view of a clamping plate and an adjustment plate of the alignment mechanism of FIG. 10.

Alignment mechanism 78 comprises a clamping plate 84, an adjustment plate 86, and an alignment fixture 88. Clamping plate 84 and adjustment plate 86 are also illustrated in FIG. 12. Clamping plate 84 includes a fixed arm 90 and a moveable arm 92. Fixed arm 90 is configured to be placed about foot 82 while moveable arm 92 may be moved outwardly and manipulated to be placed around foot 80 as shown in FIG. 11. When properly positioned, a screw 94 is tightened to lock clamping plate 84 to feet 80 and 82.

Adjustment plate 86 is coupled to clamping plate 84 so as to permit adjustment plate 86 to be moved relative to clamping plate 84. More specifically, a pair of tightening screws 96 and 98 are provided to secure clamping plate 84 to adjustment plate 86. Screws 96 and 98 are screwed into blocks 87 and 89 (see FIG. 11). Blocks 87 and 89 may travel in plate 84 in both a back and forth manner, fore and aft and permit a slight degree of yaw of plate 86 relative to plate 84. Adjustment plate 86 further includes a pair of slots 100 and 102 which serve a dual function. As shown in FIGS. 10 and 11, slots 100 and 102 permit alignment fixture 88 to be coupled to adjustment plate 86. In this way, after clamping plate 84 is secured to scanner 70, adjustment plate 86 may be moved to properly position an arm 104 of alignment fixture 88 with entry port 76. When properly aligned, screws 96 and 98 are tightened and alignment fixture 88 is removed from adjustment plate 86. A cartridge transport device may then be secured to slots 100 and 102 to securely couple the cartridge transport device with scanner 70. Moreover, by previously aligning arm 104 of alignment fixture 88 with entry port 76, the cartridge transport device will be properly aligned with scanner 70 so that cartridges may properly be inserted into and removed from entry port 76 as described hereinafter. Hence, alignment mechanism 78 provides a convenient way to couple a cartridge transport device to scanner 70 without interfering with the operation of scanner 70 or compromising the alignment of scanner 70.

Figure 13:
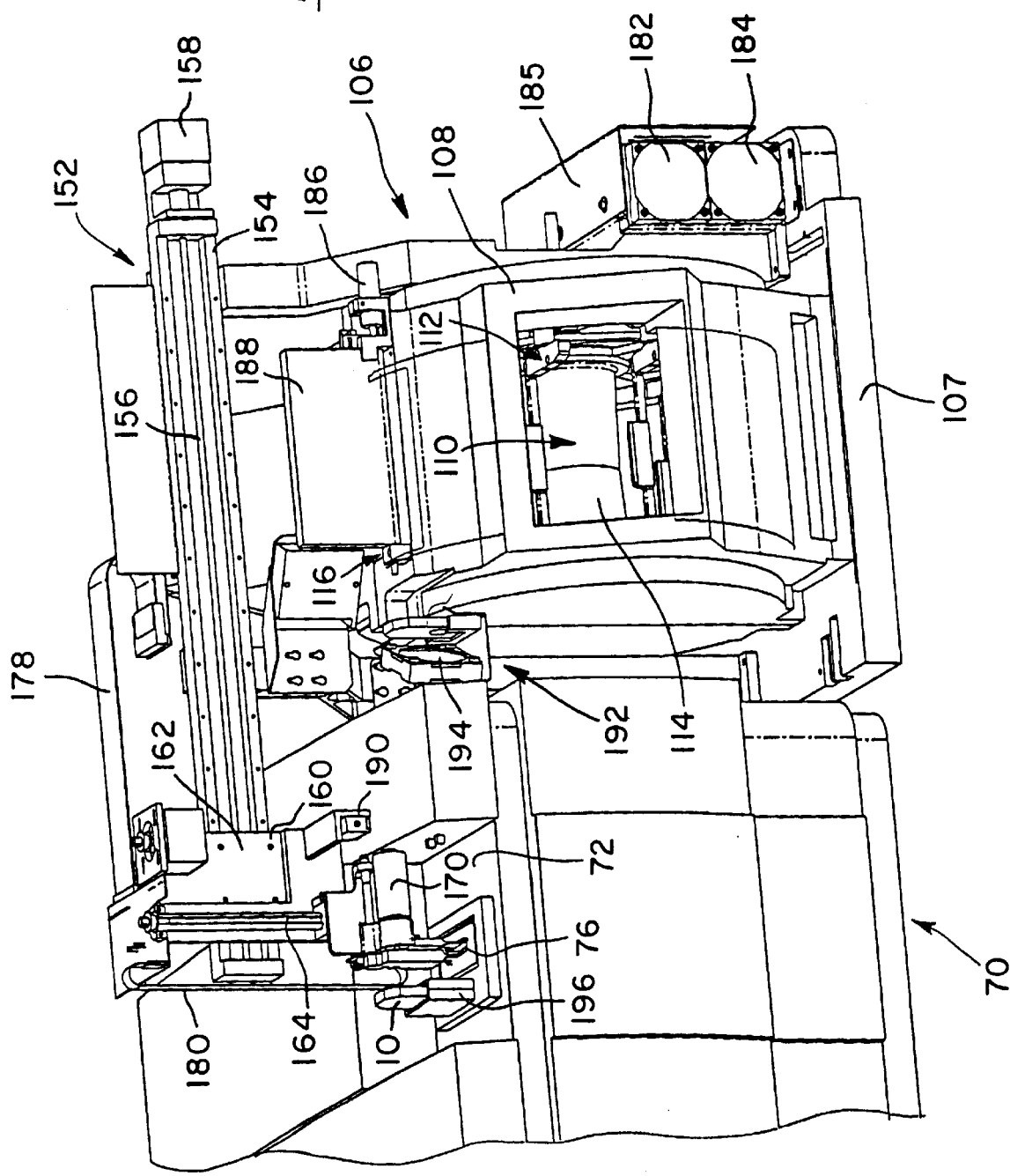
FIG. 13 is a top perspective view of a cartridge transporting device that is coupled to the scanner of FIG. 10 according to the invention.

Referring now to FIG. 13, a cartridge transport device 106 is shown coupled to scanner 70. For convenience of illustration, alignment mechanism 78 is not shown in FIG. 13. However, it will be appreciated that in operation, clamping plate 84 and adjustment plate 86 will be employed to couple scanner 70 to cartridge transport device 106 as just described.

Transport device 106 comprises a base 107 that may be coupled to adjustment plate 86 simply by sliding base 107 over adjustment plate 86. Transport device 106 further comprises a housing 108 that defines an interior 110. Housing 108 is constructed of an insulating material, such as styrofoam, to help maintain a temperature controlled environment within interior 110. Hidden from view is a thermal Peltier cooling device to provide a chilled environment within interior 110. Merely by way of example, interior 110 may be maintained at a temperature in the range from about 5° C. to about 25° C., and more preferably at about 15° C. Also hidden from view is a fan that is disposed within interior 110 to circulate air within interior 110 to maintain a generally constant temperature throughout interior 110.

Disposed within interior 110 is a rack system 112 that is configured to hold a plurality of carriers which each include multiple cartridges as described hereinafter. Conveniently, an opening 114 is provided in housing 108 to facilitate insertion and removal of the carriers. Although not shown, a cover will be placed over opening 114 when in use to maintain the temperature controlled environment within interior 110. Housing 108 further includes a top opening 116 to provide access into interior 110 when removing individual cartridges for scanning as described hereinafter.

Figure 14:
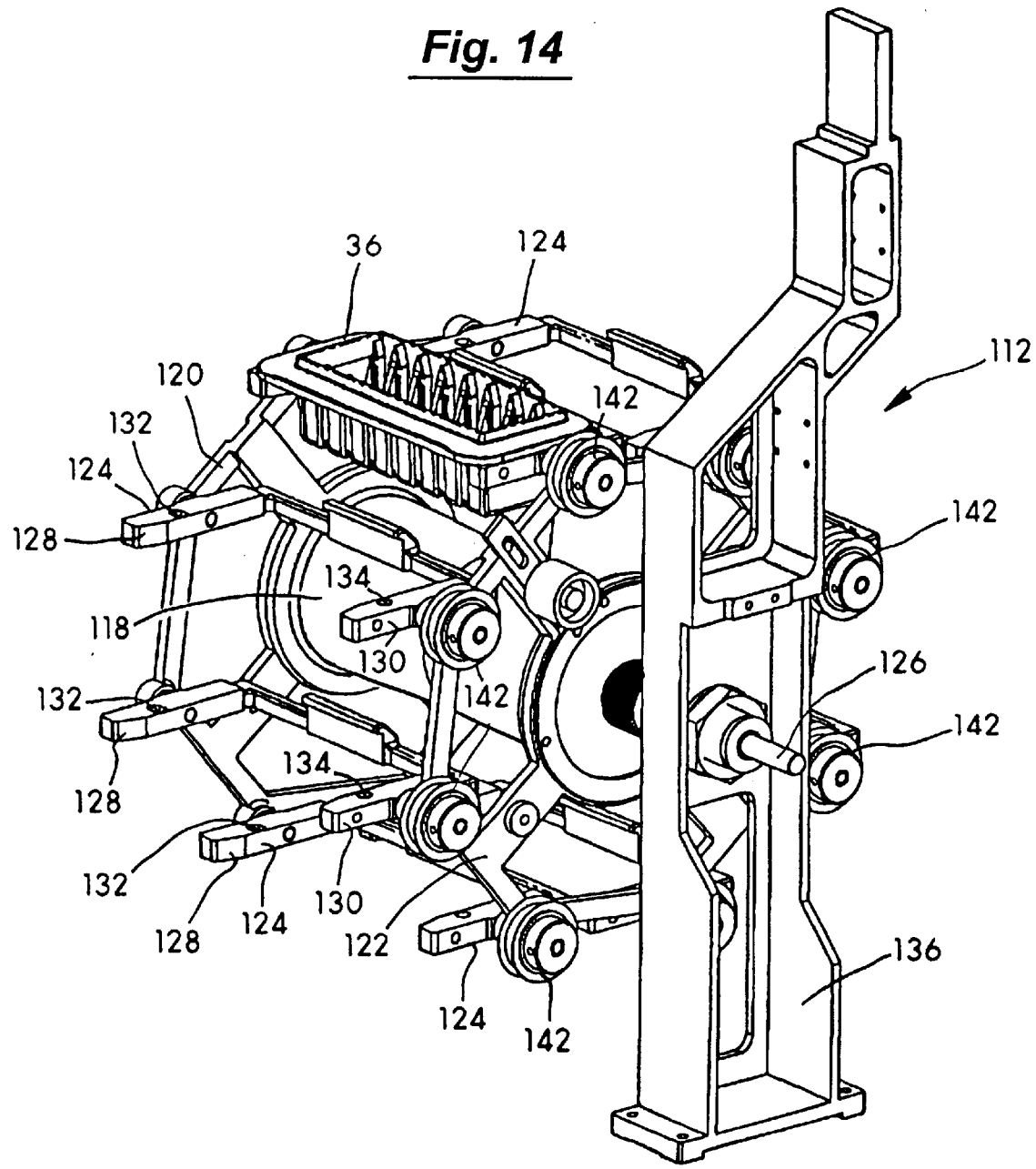
FIG. 14 is a perspective view of a rack system of the transporting device of FIG. 13.

Referring to FIG. 14, operation of rack system 112 will be described in greater detail. Rack system 112 is constructed of a rotatable drum 118 having a pair of annular extensions 120 and 122. A plurality of racks 124 are pivotally coupled between annular extensions 120 and 122. Further, a shaft 126 is employed to rotate drum 118. As drum 118 rotates, racks 124 pivot relative to extensions 120 and 122 to remain generally horizontal at all times.

Each rack 124 comprises a pair of arms 128 and 130. Arm 128 includes a hole 132 and arm 130 includes a hole 134. Each rack 124 is configured to hold a carrier 36 as previously described in connection with FIGS. 5–9. Holes 132 and 134 are offset and are configured to receive knobs 54 and 56 of carrier 36 when carrier 36 is inserted between arms 128 and 130. In this way, racks 124 are keyed so that carriers 36 may be inserted and held in only one orientation, thereby ensuring proper orientation of the cartridges which are held within carriers 36. Further, by configuring racks 124 so that they remain generally horizontal during rotation of drum 118, the top ends of carriers 36 also remain horizontal. In this way, the cartridges will not fall out of carriers 36 during rotation. Further, the cartridges will be at the proper orientation when they are ready to be removed and scanned as described hereinafter.

Hence, rack system 112 permits multiple cartridges to be held within interior 110 and provides a convenient way to advance the cartridges until they are aligned with opening 116 where they will be retrieved from housing 110 as described hereinafter. Further, by using standard carriers, multiple sets of cartridges may easily be inserted into housing 110 simply by inserting the carriers through opening 114 in housing 108 and sliding the carriers between arms 128 and 130 of racks 124 until knobs 54 and 56 fit into holes 132 and 134.

Figure 15:
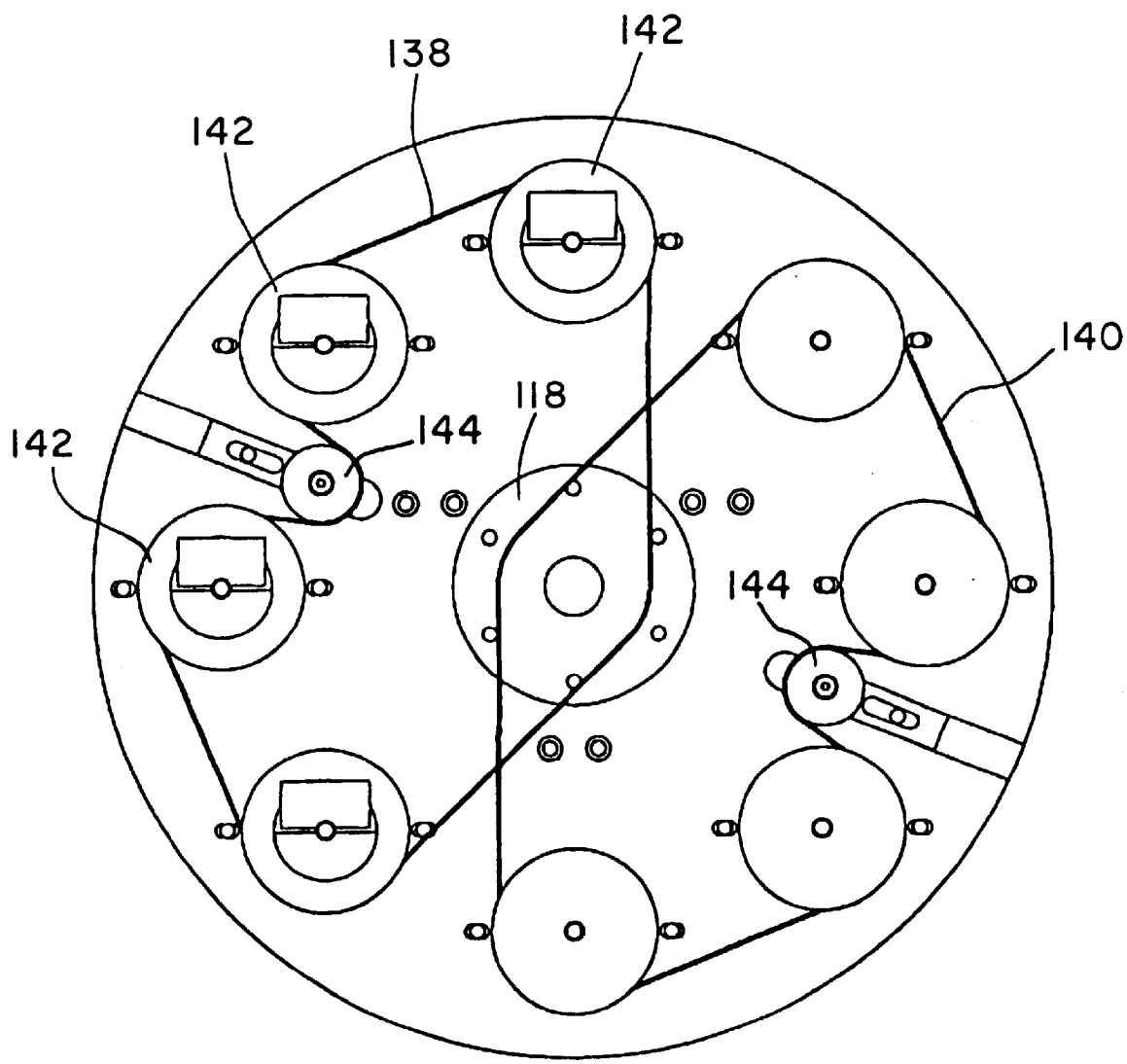
FIG. 15 is an partial end view of the rack system of FIG. 14 showing a pair of belts employed to rotate the racks.

As also shown in FIG. 14, a support 136 is employed to properly position rack system 112 within housing 108. Shaft 126 extends through support 136, and a motor and belt arrangement (not shown) is employed to rotate shaft 126. As best shown in FIG. 15, a pair of toothed belts 138 and 140 are employed to maintain racks 124 generally horizontal during rotation of drum 118. Belts 138 and 140 extend about a plurality of tooth gears 142 that in turn are coupled to annular extension 122. A set of idlers 144 are also employed to ensure racks 124 remain horizontal. Hence, as drum 118 is rotated, belts 138 and 140 travel about tooth gears 142, with idlers 144 keeping the appropriate tension to ensure that carriers remain upright during rotation.

Figure 16:
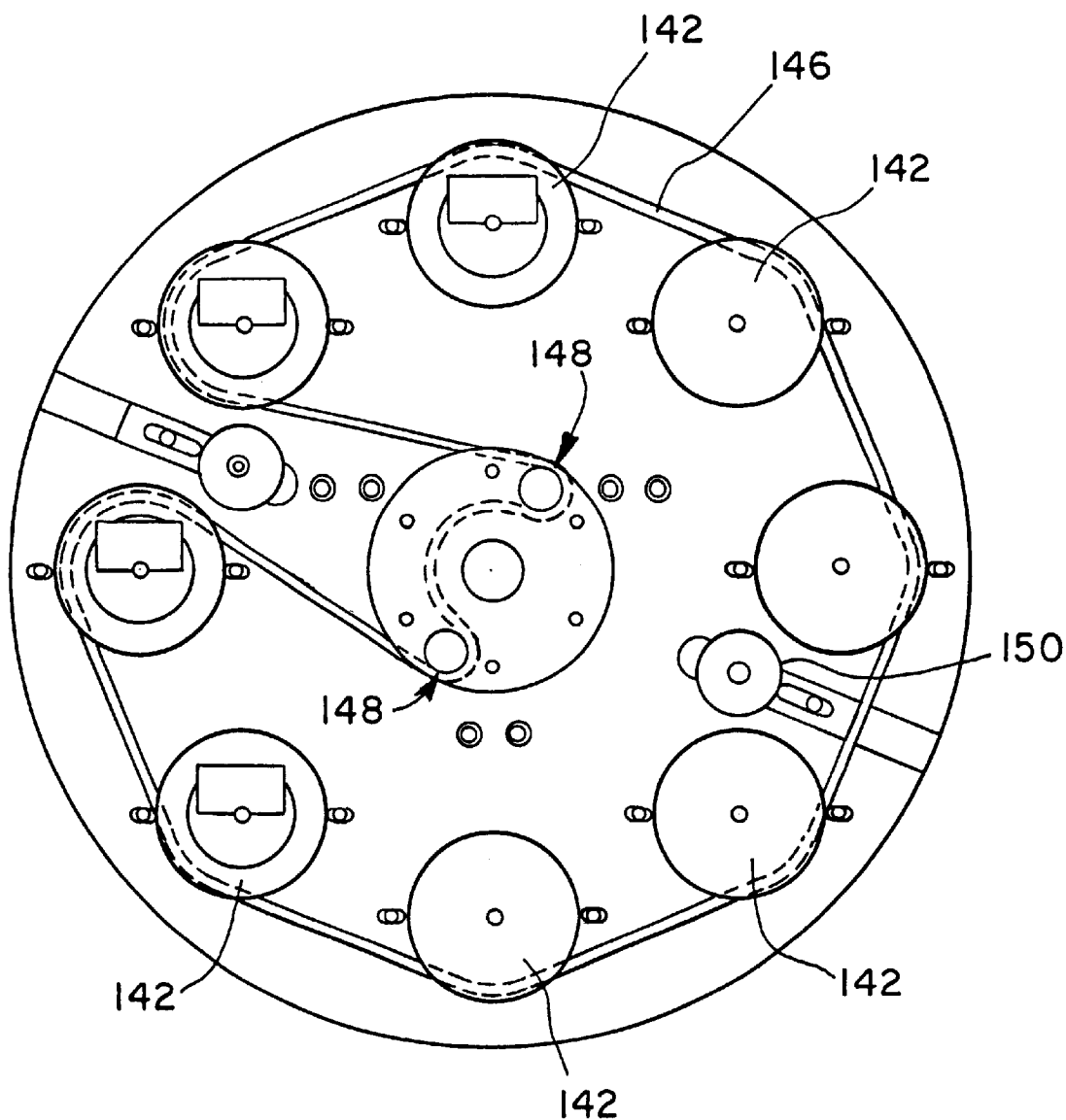
FIG. 16 illustrates the rack system of FIG. 15 with a single belt arrangement.

An alternative belt arrangement is shown in FIG. 16. In the embodiment of FIG. 16, a single belt 146 is employed. Belt 146 extends around tooth gears 142, a pair of idlers 148 and a tensioner 150. Further, although shown with a rotating rack system, it will be appreciated that other mechanism may be used to move the cartridge holders to provide access to the cartridges. For example, the cartridge holders may be translated within the chamber. Furthermore, although a system of belts for rotating the rack system has been described, it will be appreciated that other arrangements may also be used. For example, a system of chains, gears, flexible couplings (such as Oldham couplings), bellows couplings, Helical brand flexible bar couplings and the like may also be used.

Figure 17:
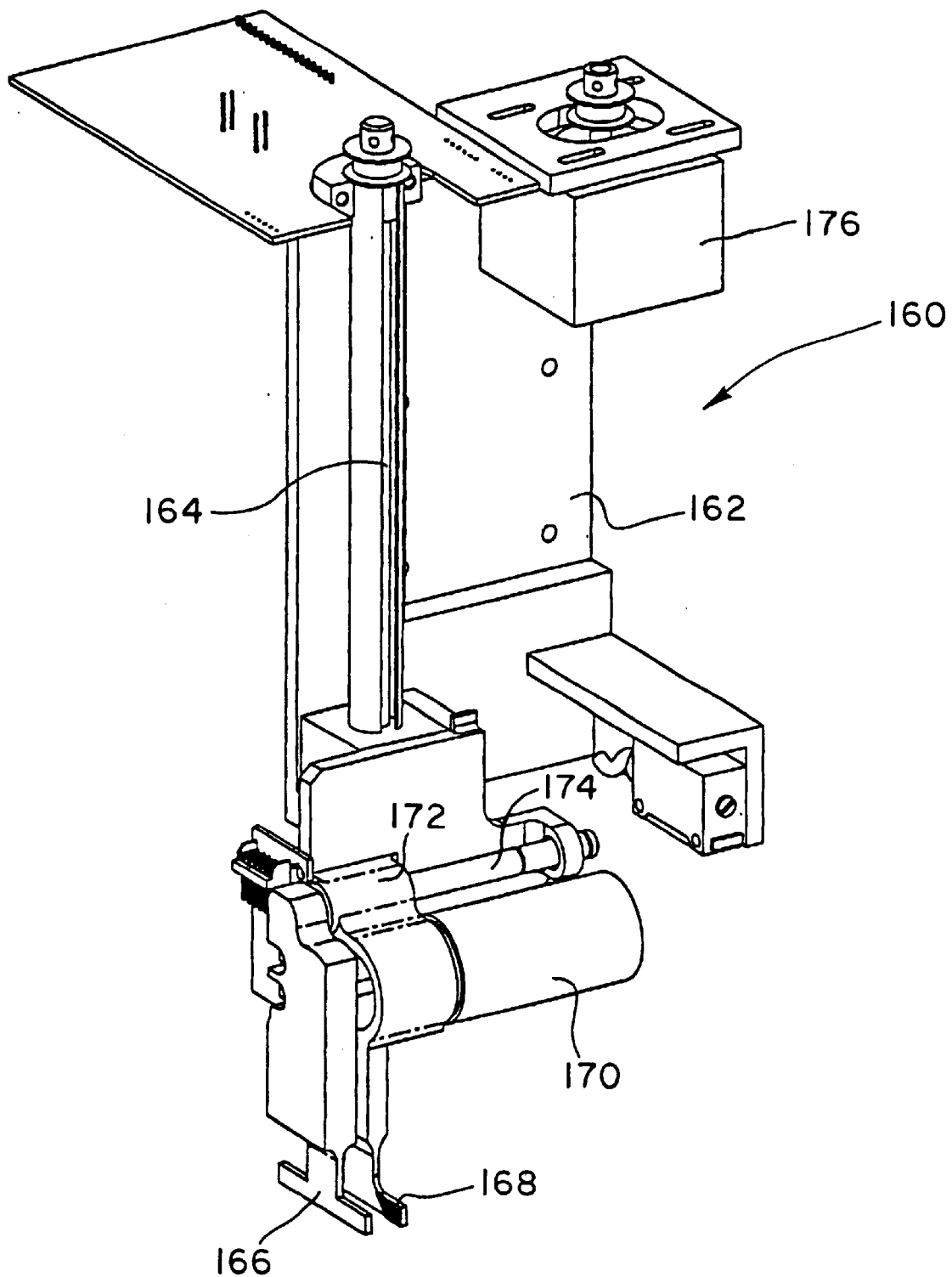
FIG. 17 is a perspective view of a grasping mechanism and vertical lead screw of the device of FIG. 13.
Figure 18:
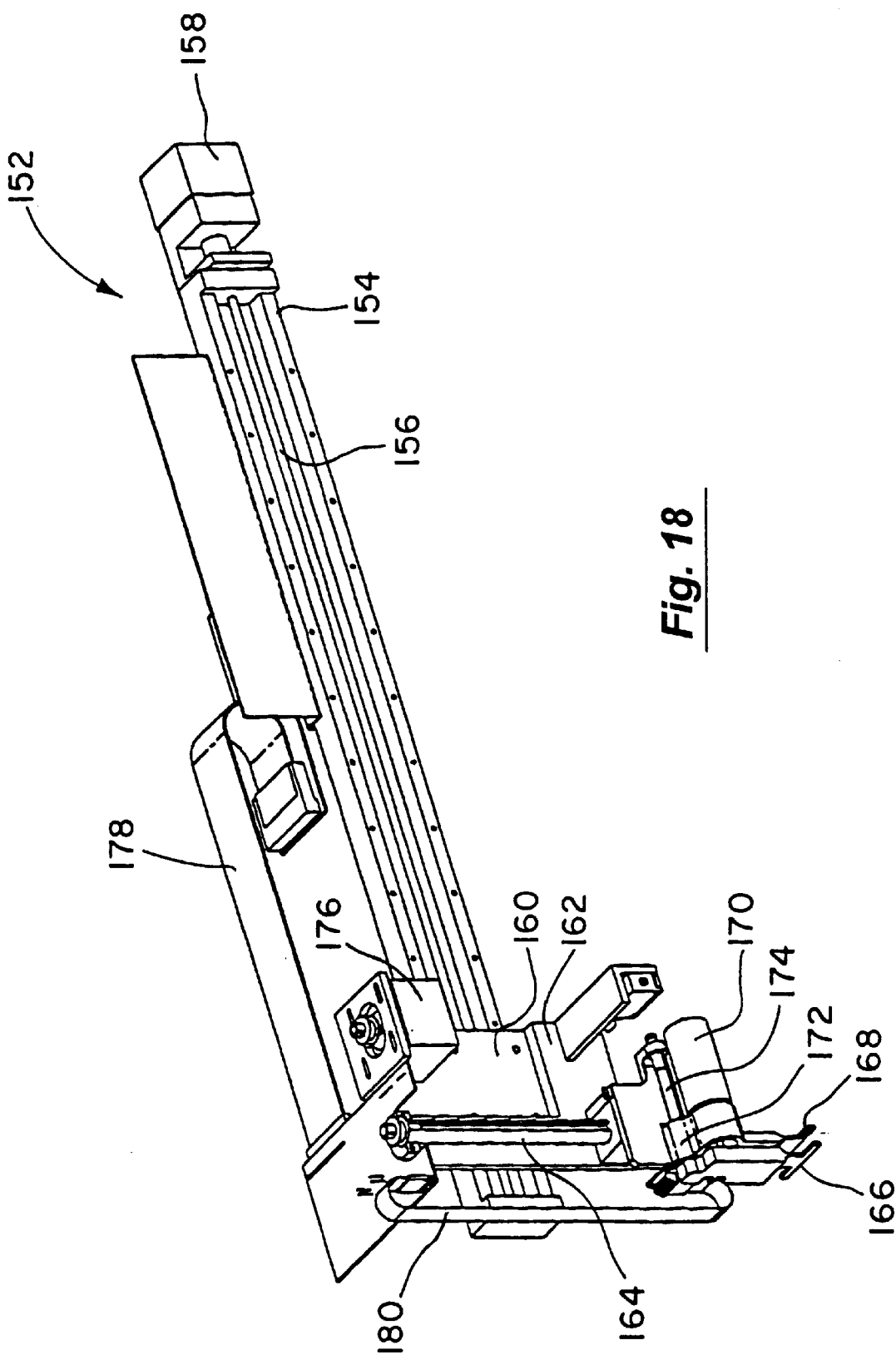
FIG. 18 is a perspective view of the grasping mechanism and vertical lead screw of FIG. 17 along with a horizontal lead screw.
Figure 19A:
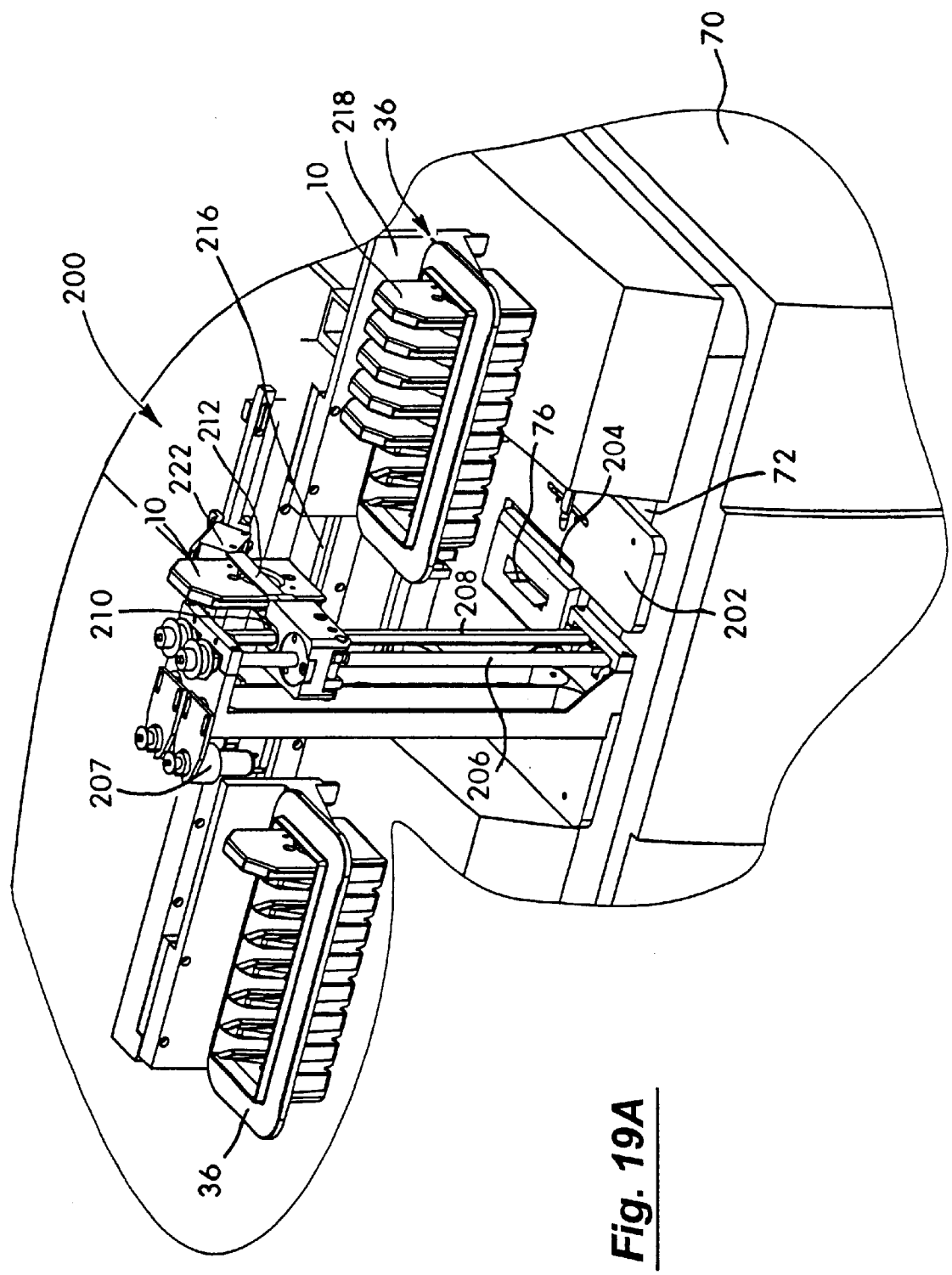
FIG. 19A is a perspective view of a scanner having an alternative cartridge transporting device according to the invention.
Figure 19B:
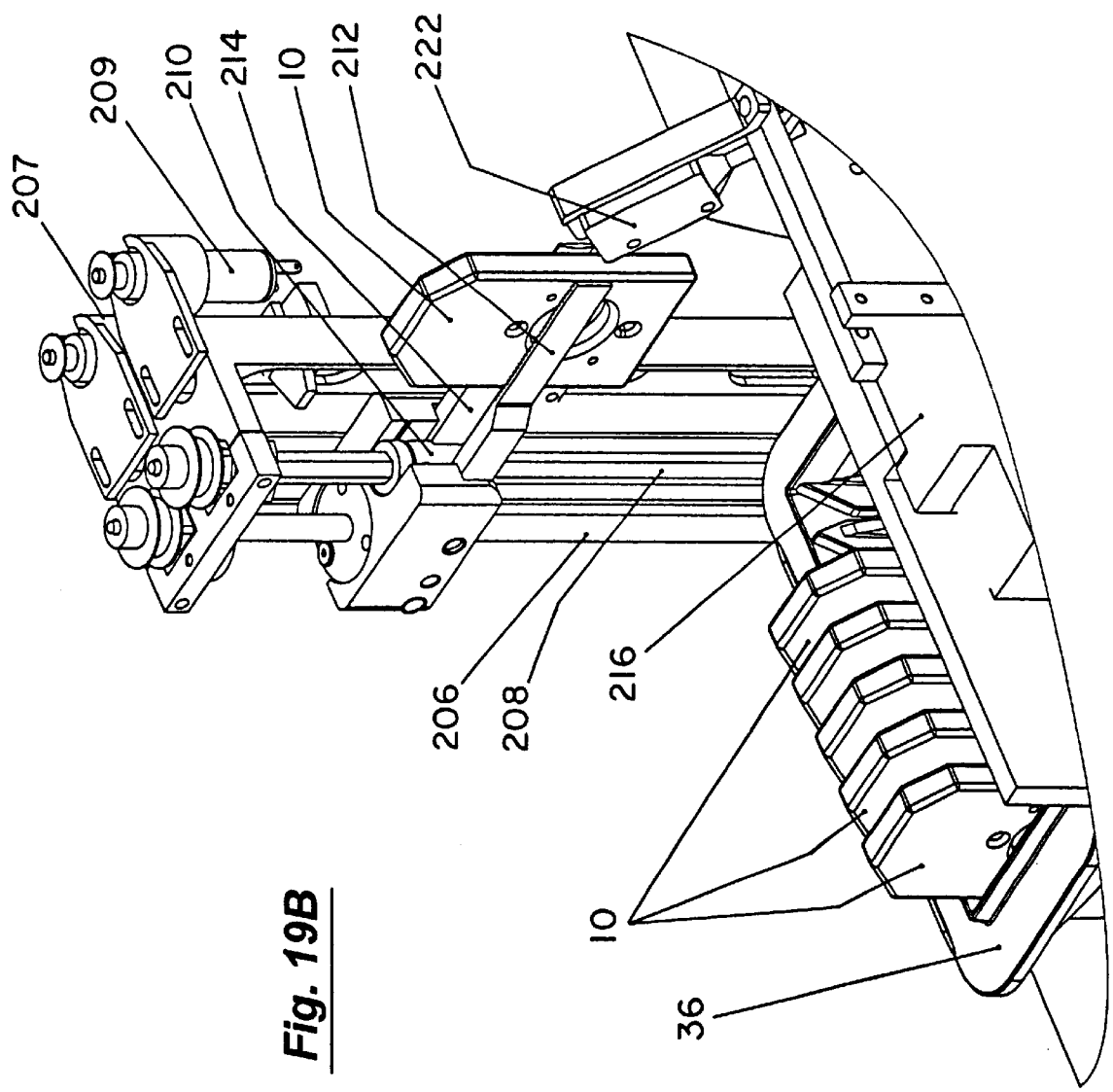
FIG. 19B is a more detailed rear perspective view of the scanner of FIG. 19A.
Figure 20:
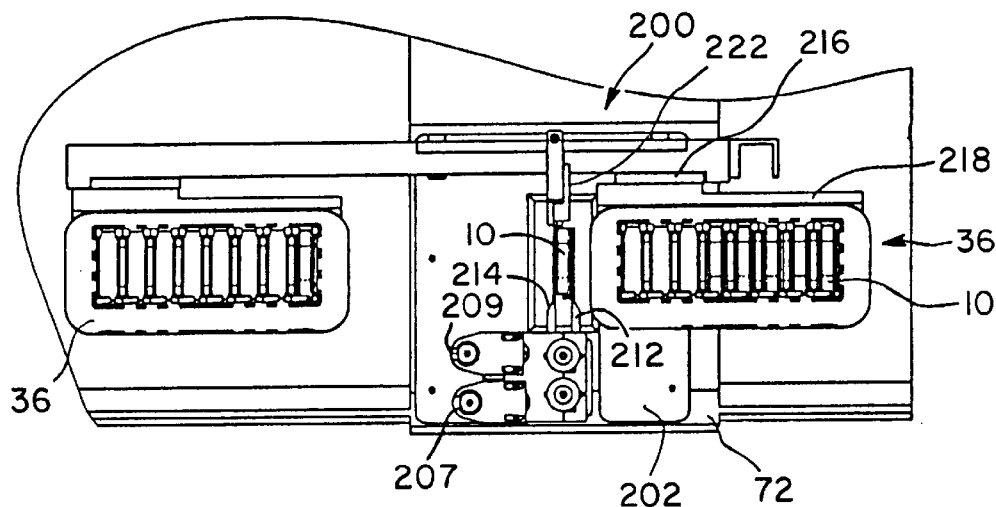
FIG. 20 is a top view of the scanner and transporting device of FIG. 19.
Figure 22:
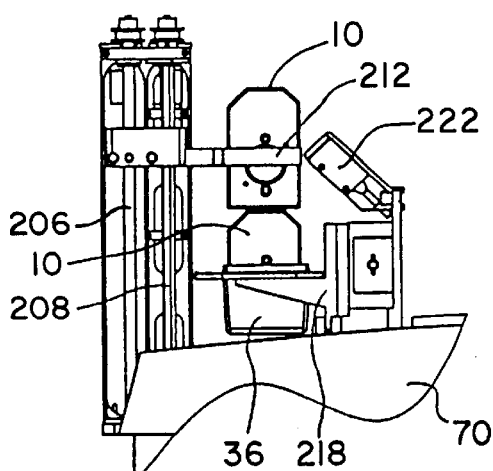
FIG. 22 is an end view of the scanner and transporting device of FIG. 19.
Figure 21:
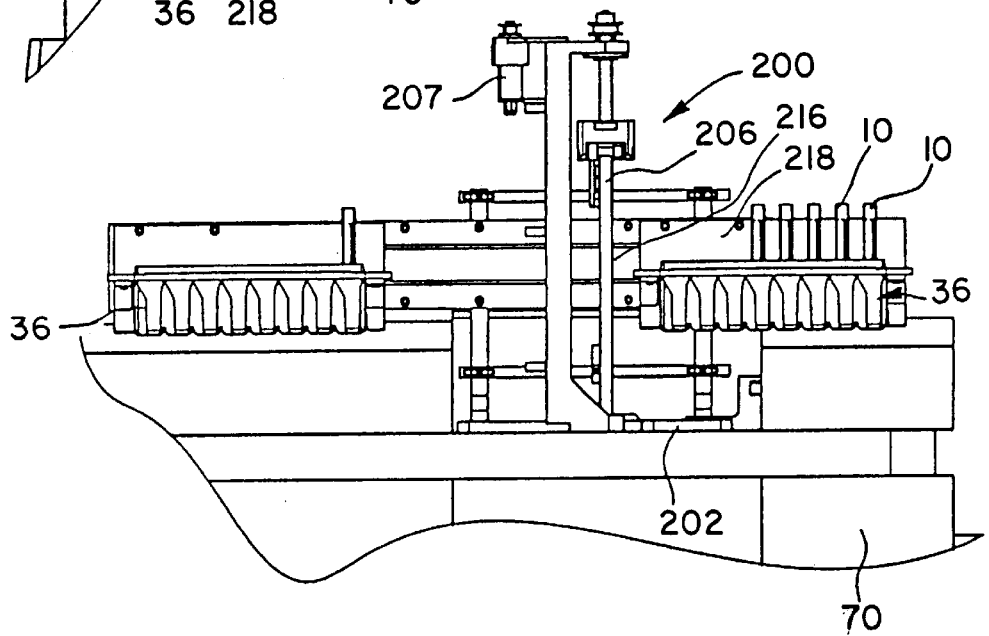
FIG. 21 is a front view of the scanner and transporting device of FIG. 19.

Referring now to FIG. 18 in connection with FIG. 13, a transport system 152 for moving cartridges between housing 108 and scanner 70 will be described. Transport system 152 comprises a horizontal support 154 that is coupled to housing 108. Horizontal support 154 holds a horizontal lead screw 156 that is rotated by a DC servo motor 158. Alternatively, a stepper motor may be used. Slidably coupled to horizontal support 154 is a grasping mechanism 160 which is also shown in FIG. 17. Grasping mechanism 160 comprises a vertical support 162 that holds a vertical lead screw 164. In turn, lead screw 164 is employed to vertically move a pair of grasping fingers 166 and 168. Also coupled to support 162 is a pneumatic cylinder or electric solenoid 170. Coupled about solenoid 170 is a collar 172 through which a rail 174 extends. In turn, rail 174 is coupled to finger 166 to facilitate movement of finger 166 relative to finger 168 when solenoid 170 is actuated. Further, a DC servo motor 176 (or a stepper motor) is coupled to support 162 and is employed to rotate lead screw 164.

In operation, motor 158 is actuated to turn lead screw 156. This in turn moves grasping mechanism 160 horizontally side to side depending on the direction of rotation of lead screw 156. Motor 176 is operated to rotate lead screw 164 to raise or lower grasping fingers 166 and 168 depending on the direction of rotation of lead screw 164. Solenoid 170 may be actuated to move fingers 166 and 168 relative to each other to grasp or release a cartridge depending on the direction of movement of solenoid 170. Conveniently, transport device 106 may include a printed circuit board having controlling circuitry to operate the various motors and solenoid. Wiring 178 permits an electrical connection between the PC board and the components of grasping mechanism 160. Similarly, wiring 180 provides the appropriate electrical connection between the PC board and solenoid 170. Similar wiring may be employed for motor 158. A power supply 185 is also provided to supply power to the various electrical components of transport device 106. As best shown in FIG. 13, fans 182 and 184 are employed to cool the power supply.

As previously described, lead screws may be employed to horizontally and vertically translate grasping mechanism 160. However, it will be appreciated that other translation mechanisms may be used as well. For example, a system of belts could also be employed.

Referring back to FIG. 13, cartridge transport device 106 further includes a rotary solenoid 186 that is coupled to a lid 188. Solenoid 186 is actuated to place lid 188 over opening 116 and to remove lid 188 from opening 116. In this way, interior 110 may remain closed until a cartridge is ready to be inserted into or removed from housing 110. At this point, a signal is sent to rotary solenoid 186 which opens lid 188 to permit access into interior 110. Alternatively, a variety of other opening mechanisms may be employed. For example, lid 188 may be configured to slide over opening 116. In such a case, grasping mechanism 160 may include a magnet 190 for interacting with corresponding magnet on lid 188. In this way, as grasping mechanism 160 is horizontally translated, magnet 190 will attach to the magnet on lid 188 to slide lid 188 open. Conversely, when grasping mechanism 160 is translated the opposite direction, lid 188 will be pulled across opening 116.

Cartridge transport device 106 further includes a warming station 192 for warming cartridge 10 after being removed from housing 110. Warming of cartridge 10 is desirable in that it helps to eliminate condensation on the cartridge before it enters into scanner 70. Warming station 192 includes a fan 194 that is employed to blow ambient air across cartridge 10 to warm cartridge 10 before entering scanner 70.

Disposed adjacent entry port 76 is a holding station 196 that is employed to hold one of cartridges 10 after it has been removed from scanner 70. Holding station 196 is optional and serves to increase the throughput of cartridges that are scanned with scanner 70 as described hereinafter.

In operation, rack system 112 is employed to align a set of cartridges 10 which are held within a carrier 36 with opening 116. Grasping mechanism 160 is then positioned over opening 116 using lead screw 156. Grasping mechanism 160 is lowered into housing 110 using lead screw 164 until grasping fingers 166 and 168 are disposed on either side of one of the cartridges 10. Solenoid 170 is then actuated to move grasping fingers 166 and 168 together to grasp the cartridge. The cartridge is then raised from housing 110 by rotating lead screw 164 in the opposite direction. Conveniently, cartridge 10 may include a barcode label which identifies the particular cartridge. Further, a barcode reader (not shown) may be disposed within housing 110 to read the barcode label as the cartridge is being removed from housing 108. Use of carriers 36 is advantageous in that they properly align the cartridges so that the label may be read by the barcode reader and so that the cartridges will be in the proper orientation when being inserted into entry port 76 of scanner 70.

After cartridge 10 has been removed from housing 108, it is taken to warming station 192 where it is warmed by air produced from fan 194. After sufficient warming, cartridge 10 is again grasped by grasping mechanism 160 and moved into entry port 76 of scanner 70. Following scanning, grasping mechanism 160 is employed to remove cartridge 10 from scanner 70. Grasping mechanism 160 may then be moved back over opening 116, to place cartridge 10 back into housing 108 after lid 188 has been opened.

Alternatively, to reduce the cycle time, the cartridge may be placed into holding station 196 after exiting scanner 70. In this way, after depositing cartridge 10 in holding station 196, grasping mechanism 160 may be moved back to warming station 194 to remove a cartridge that had previously been placed into warming station 194. Cartridge 10 is then removed from warming station 194 and placed into entry port 76 of scanner 70 allowing scanning to commence. Grasping mechanism 160 then grasps the cartridge that is held within holding station 196 and returns it back to housing 108. Grasping mechanism 160 then removes another cartridge from housing 108 and places it into the empty warming station. Grasping mechanism 160 is then moved back to warming station 194 where the above described process is repeated. In this way, the operation of grasping mechanism 160 is partially overlapped with scanning to increase the number of cartridges that may be scanned within a given time period.

The PC board may be configured to control all of the operations so that scanning takes place in a fully automated manner. Conveniently, a computer having a display screen may be coupled to the PC board and may include a networking interface to permit convenient interaction with the scanner and transport device. Further, the host computer may include appropriate display screens to permit manual operation of any of the above steps and to permit tracking of a specific cartridge based on the barcode information.

Referring now to FIGS. 19–22, an alternative embodiment of a cartridge transport system 200 that may be used with scanner 70 will be described. System 200 comprises an alignment plate 202 that is secured to fit on top end 72 of scanner 70 as shown. Plate 202 includes an opening 204 that is configured to be placed about entry port 76 when plate 202 is properly positioned. Extending from plate 202 is a vertical lift shaft 206 and a guide shaft 208. Disposed about shaft 208 is a cam follower 210 having a pair of arms 212 and 214 for grasping cartridge 10. Shaft 206 may be constructed as a lead screw and may be coupled to a motor 207. In this way, rotation of shaft 206 causes arms 212 and 214 to be vertically raised and lowered to permit cartridge 10 to be deposited into and withdrawn from entry port 76. Further, vertical movement may be used to insert cartridges 10 into and from carrier 36. Shaft 208 is configured as a hexagonal shaft and is rotated by a motor 209. In this way, rotation of shaft 208 causes arms 212 and 214 to move relative to each other to permit grasping and releasing of one of the cartridges. Conveniently, one of arms 212 or 214 may be rounded while the other is serrated to facilitate grasping of cartridges 10. Optionally, a sensor 222 may be provided to detect when cartridge 10 has been properly grasped.

Also coupled to scanner 70 is a track 216 to which a carrier frame 218 is coupled. Frame 218 is configured to hold a carrier 36 which in turn holds a set of cartridges 10 as shown. Frame 218 is slidable along track 216 to permit carrier 36 to be moved relative to arms 212 and 214 when an appropriate cartridge needs to be removed from or inserted into carrier 36. Conveniently, a motor (not shown) may be used to translate frame 218 horizontally along track 216. Although shown holding two carriers 36, it will be appreciated that in operation only a single carrier 36 may be used.

In operation, carrier 36 is moved along track 216 until a first one of the cartridges 10 is aligned with arms 212 and 214. Shaft 206 is then rotated to lower arms 212 and 214 until positioned about the first cartridge. Shaft 208 may then be rotated to move arms 212 and 214 close together until they grasp the cartridge. Carrier 36 may then be moved along track 216 so as to be clear of entry port 76. Lead screw 206 is rotated to lower cartridge 10 into entry port 76. Shaft 208 is rotated to release arms 212 and 214. Following scanning, the reverse procedure is followed to remove cartridge 10 from scanner 70 and to place it back into carrier 36. The process is then repeated for the remaining cartridges within carrier 36.

Hence, the invention provides exemplary techniques for transporting cartridges to and from a scanner. Conveniently, the invention may utilize standardized carriers that hold a number of cartridges that may be stored in a cool chamber. A two-axis robot may be employed to move the cartridges to and from the scanner, a warming station, and a holding station. A local operator interface and network connection may be provided to a host work station to facilitate operation of the transport system.

Use of the cartridge carriers is advantageous in that they provide a standardized way to hold the multiple cartridges. Further, the cartridge carriers may include keyed slots to prevent reverse installation. Use of the housing having a chilled chamber permits storage of the cartridges for several hours prior to scanning. However, it will be appreciated that in some embodiments, a temperature controlled chamber may not be needed. Following removal, the warming station may be used to eliminate condensation on the cartridge before its insertion into the scanner. Also, use of the robot allows automated movement of the cartridges between the carriers and the various stations in the scanner. Conveniently, a barcode scanner may be employed to identify the cartridge contents to the host computer. In one aspect, a connection may be made to the transport system using a network interface, and a local user interface may be incorporated to facilitate loading and unloading of the cartridges. Further, a non-intrusive alignment mechanism may be used to non-intrusively couple to the scanner. The alignment mechanism may then be used as the sole contact for alignment between the cartridge loader and the scanner. Conveniently, the cartridge loader may be configured to be relatively small in size so as to fit on a bench top and be installable by a single person.

The invention has been described in detail for purposes of clarity of understanding. However, it will be appreciated that certain changes and modifications may be practiced within the scope of the appended claims.

What is claimed is:

1. An apparatus, comprising:
   a scanner instrument that is constructed and arranged to scan one or more probe arrays;
   a transporter constructed and arranged to transport the probe arrays to the scanner instrument and provide the probe arrays for loading into the scanner instrument; and
   a carrier for holding a plurality of probe arrays, wherein the carrier has a first end and an open second end, and a plurality of slots that are configured to receive the probe arrays;
   wherein the transporter is configured to transport the probe arrays directly from the carrier and into the scanner instrument.

2. An apparatus as in claim 1, wherein the probe array is disposed on a substrate, and wherein the substrate is coupled to a housing.

3. An apparatus as in claim 2, further comprising a carrier that is adapted to hold a plurality of housings that each have a substrate and at least one of the probe arrays.

4. An apparatus as in claim 3, wherein the carrier is configured to hold each housing in a generally vertical orientation.

5. An apparatus as in claim 3, wherein the carrier is configured to hold each housing spaced apart from each other.

6. An apparatus as in claim 1, wherein the carrier is mechanically coupled to the scanner instrument.

7. An apparatus as in claim 1, wherein the carrier is housed within a housing.

8. An apparatus as in claim 1, wherein the transporter comprises a grasping mechanism.

9. An apparatus as in claim 8, wherein the grasping mechanism comprises a pair of fingers that are movable toward and away from each other.

10. An apparatus as in claim 1, wherein the transporter is configured to move the probe arrays in an axial direction from the carrier and into the scanner.

11. An apparatus as in clam 1, wherein the transporter is configured to advance the carrier each time a new one of the probe arrays is transported.

12. An apparatus as in claim 1, further comprising a barcode reader disposed within the scanner.

13. An apparatus as in claim 12, wherein each probe array is held on a substrate that includes an associated bar code to uniquely identify the probe array.

14. An apparatus as in claim 1, further comprising a controller to control the transporter.

15. An apparatus as in claim 1, wherein the probes includes those selected from a group consisting of agonists and antagonists for cell membrane receptors, toxins and venoms, viral epitopes, hormones, hormone receptors, peptides, enzymes, enzyme substrates, cofactors, drugs, lectins, sugars, oligonucleotides or nucleic acids, oligosaccharides, proteins, and monoclonal antibodies.

16. A method for transporting probe arrays, the method comprising:
   providing a scanner;
   transporting one or more probe arrays using a transporter to the scanner for loading into the scanner; and
   removing the probe array from the scanner, returning the probe array to a carrier and placing another probe array into the scanner using the transporter.

17. A method as in claim 16, wherein the probe array is disposed on a substrate which is coupled to a housing, and further comprising transporting the housing from the carrier to the scanner.

18. A method as in claim 17, wherein the housing is held in a generally vertical orientation in the carrier, and moving the housing out of the carrier in a generally vertical orientation.

19. A method as in claim 17, wherein the carrier holds multiple housings in a spaced apart configuration to permit access to each housing by the transporter, and moving the housing out of the carrier while being spaced apart from the other housings.

20. A method as in claim 17, where in the carrier has a bottom end and an open top end, and a plurality of slots that are configured to receive multiple housings, and further comprising transporting the probe arrays in an axial direction from the carrier and into the scanner.

21. A method as in claim 17, further comprising moving the substrate directly from the carrier and into the scanner.

22. A method as in claim 16, further comprising advancing the carrier to align the next probe array with the transporter.

23. A method as in claim 16, further comprising reading a barcode label associated with the probe array to identify the probe array.

24. A method for transporting probe arrays, the method comprising:
providing a scanner;
providing one or more probe arrays that are disposed on a substrate that is coupled to a housing; and
transporting the housing using a transporter to the scanner for loading into the scanner, removing the housing from the scanner, returning the housing to a carrier and placing another housing into the scanner using the transporter.

25. A system, comprising:
one or more probe arrays that are disposed on one or more substrates;
one or more housings configured and arranged to house the probe arrays;
a carrier configured and arranged to hold the housings such that the substrates are disposed in a generally vertical orientation;
a scanner configured and arranged to scan one or more of the probe arrays; and
a transporter configured and arranged to transport the probe arrays from the carrier to the scanner;
wherein the transporter is configured to transport the probe arrays directly from the carrier and into the scanner.

26. A system as in claim 25, further comprising a barcode reader disposed to read a barcode associated with at least one probe.

27. A system as in claim 25, wherein the grasping mechanism comprises a pair of fingers that are movable toward and away from each other.

28. A system as in claim 27, wherein the barcode reader is disposed within the scanner.

29. A system as in claim 27, wherein at least one substrate is associated with a bar code to uniquely identify one or more probe arrays disposed on the substrate.

30. A system as in claim 29, wherein the barcode is disposed on a housing that houses the substrate.

31. A system as in claim 27, wherein the bar code is disposed on the substrate.

32. A system as in claim 25, further comprising a controller to control the transporter.

33. A system, comprising:
one or more probe arrays that are disposed on one or more substrates;
one or more housings configured and arranged to house the probe arrays;
a carrier configured and arranged to hold the housings such that the substrates are disposed in a generally vertical orientation;
a scanner configured and arranged to scan one or more of the probe arrays;
a transporter configured and arranged to transport the probe arrays from the carrier to the scanner; and
a barcode reader disposed to read a barcode associated with at least one probe, wherein the barcode reader is disposed within the scanner.

34. A system, comprising:
one or more probe arrays that are disposed on one or more substrates;
one or more housings configured and arranged to house the probe arrays;
a carrier configured and arranged to hold the housings such that the substrates are disposed in a generally vertical orientation;
a scanner configured and arranged to scan one or more of the probe arrays;
a transporter configured and arranged to transport the probe arrays from the carrier to the scanner; and
a barcode reader disposed to read a barcode associated with at least one probe, wherein each substrate is associated with a bar code to uniquely identify one or more probe arrays disposed on the substrate.

35. A system as in claim 34, wherein the bar code is disposed on the substrate.

36. A system as in claim 34, wherein the barcode is disposed on a housing that houses the substrate.

37. An apparatus, comprising:
a carrier that is configured and arranged to hold a plurality of housings, wherein each housing is configured and arranged to include one or more substrates and one or more probe arrays that are disposed on the substrates, and wherein the carrier is further configured and arranged to hold each of the substrates in a generally vertical orientation;
a scanner that is configured and arranged to scan one or more of the probe arrays; and
a transporter configured and arranged to transport the probe arrays directly from the carrier to the scanner.

38. An apparatus as in claim 37, wherein the carrier is configured and arranged to advance to provide a second probe array for transportation to the scanner after a first probe array has been transported from the carrier to the scanner and returned from the scanner to the carrier.

39. An apparatus as in claim 38, further comprising a barcode reader disposed to read a barcode associated with at least one probe array.

40. An apparatus, comprising:
a carrier that is configured and arranged to hold a plurality of housings, wherein each housing is configured and arranged to include one or more substrates and one or more probe arrays that are disposed on the substrates, and wherein the carrier is further configured and arranged to hold each of the substrates in a generally vertical orientation;
a scanner that is configured and arranged to scan one or more of the probe arrays;
a transporter configured and arranged to transport the probe arrays from the carrier to the scanner; and
a barcode reader disposed to read a barcode associated with at least one probe, wherein the barcode reader is disposed within the scanner.

41. An apparatus, comprising:
a carrier that is configured and arranged to hold a plurality of housings, wherein each housing is configured and arranged to include one or more substrates and one or more probe arrays that are disposed on the substrates, and wherein the carrier is further configured and arranged to hold each of the substrates in a generally vertical orientation;
a scanner that is configured and arranged to scan one or more of the probe arrays;

a transporter configured and arranged to transport the probe arrays from the carrier to the scanner; and wherein each substrate is associated with a bar code to uniquely identify one or more probe arrays disposed on the substrate.

42. An apparatus, comprising:

a carrier that is configured and arranged to hold a plurality of housings, wherein each housing is configured and arranged to include one or more substrates and one or more probe arrays that are disposed on the substrates, and wherein the carrier is further configured and arranged to hold each of the substrates in a generally vertical orientation;

a scanner that is configured and arranged to scan one or more of the probe arrays;

a transporter configured and arranged to transport the probe arrays from the carrier to the scanner; and wherein the bar code is disposed on the substrate.

43. An apparatus, comprising:

a carrier that is configured and arranged to hold a plurality of housings, wherein each housing is configured and arranged to include one or more substrates and one or more probe arrays that are disposed on the substrates, and wherein the carrier is further configured and arranged to hold each of the substrates in a generally vertical orientation;

a scanner that is configured and arranged to scan one or more of the probe arrays;

a transporter configured and arranged to transport the probe arrays from the carrier to the scanner; and wherein the barcode is disposed on a housing that houses the substrate.

44. A method for transporting probe arrays, the method comprising:

providing a scanner;

providing a carrier that holds a plurality of housings, wherein each housing includes one or more substrates and one or more probe arrays that are disposed on the substrates, and wherein the carrier holds each of the substrates in a generally vertical orientation;

transporting one or more of the housings having the probe arrays using a transporter to the scanner for loading into the scanner by moving the housing having the probe array directly from the carrier and into the scanner.

45. An apparatus, comprising:

a scanner instrument constructed and arranged to scan one or more probe arrays;

a transporter constructed and arranged to transport the probe arrays to the scanner instrument and provide the probe arrays for loading into the scanner instrument; and a carrier for holding a plurality of probe arrays, wherein the carrier is mechanically coupled to the scanner instrument.

* * * * *